(12) United States Patent
Mault

(10) Patent No.: US 6,517,496 B1
(45) Date of Patent: Feb. 11, 2003

(54) AIRWAY-BASED CARDIAC OUTPUT MONITOR AND METHODS FOR USING SAME

(75) Inventor: James R. Mault, Evergreen, CO (US)

(73) Assignee: HealtheTech, Inc., Golden, CO (US)

(*) Notice: Subject to any disclaimer, the term of this patent is extended or adjusted under 35 U.S.C. 154(b) by 0 days.

(21) Appl. No.: 09/674,899
(22) PCT Filed: May 10, 2000
(86) PCT No.: PCT/US00/12745
§ 371 (c)(1), (2), (4) Date: Nov. 7, 2000
(87) PCT Pub. No.: WO00/67634
PCT Pub. Date: Nov. 16, 2000

Related U.S. Application Data
(60) Provisional application No. 60/133,685, filed on May 10, 1999.

(51) Int. Cl.[7] .................................................. A61B 5/08
(52) U.S. Cl. .......................... 600/532; 600/538; 600/529
(58) Field of Search .................................. 600/529–543, 600/526

(56) References Cited

U.S. PATENT DOCUMENTS

| | | |
|---|---|---|
| 2,630,798 A | 3/1953 | White et al. |
| 2,826,912 A | 3/1958 | Kritz |
| 2,831,348 A | 4/1958 | Kritz |
| 2,838,399 A | 6/1958 | Vogel, Jr. |
| 2,869,357 A | 11/1959 | Kritz |
| 2,911,825 A | 11/1959 | Kritz |
| 2,920,012 A | 1/1960 | Sanders et al. |
| 3,213,684 A | 10/1965 | Seaton et al. |
| 3,220,255 A | 11/1965 | Scranton et al. |
| 3,250,270 A | 5/1966 | Bloom |
| 3,306,283 A | 2/1967 | Arp |
| 3,523,529 A | 8/1970 | Kissen |
| 3,527,205 A | 9/1970 | Jones |
| 3,681,197 A | 8/1972 | Smith |

(List continued on next page.)

FOREIGN PATENT DOCUMENTS

| | | |
|---|---|---|
| DE | 198 10 476 | 9/1998 |
| EP | 0459647 A2 | 12/1991 |
| EP | 0 712 638 | 12/1995 |
| GB | 2323292 | 9/1998 |
| WO | WO 96/40340 | 12/1996 |

OTHER PUBLICATIONS

Medical Progress Through Technology, vol. 9, No. 1, 1982 Berlin (D), pp. 27–32, R. Salminen et al., "Computerized Breath–By–Breath Analysis of Respiratory Variables During Exercise."

(List continued on next page.)

Primary Examiner—Max Hindenburg
Assistant Examiner—Navin Natnithithadha
(74) Attorney, Agent, or Firm—Gifford, Krass, Groh, Sprinkle, Anderson & Citkowski, P.C.

(57) ABSTRACT

A respiratory gas analyzer for measuring the cardiac output of a subject includes a flow meter and an oxygen sensor interconnected with one another between a mouthpiece and a source of respiratory gases, which may be a controlled source or the atmosphere. An oximeter provides measurements of the oxygen saturation of the subject. A computer connected to receive the signals from the flow meter, oxygen sensor, and oximeter can then calculate the subject's cardiac output.

22 Claims, 3 Drawing Sheets

U.S. PATENT DOCUMENTS

| | | |
|---|---|---|
| 3,726,270 A | 4/1973 | Griffis et al. |
| 3,797,480 A | 3/1974 | Williams |
| 3,799,149 A | 3/1974 | Rummel et al. |
| 3,814,091 A | 6/1974 | Henkin |
| 3,834,375 A | 9/1974 | Sanctuary et al. |
| 3,895,630 A | 7/1975 | Bachman |
| 3,938,551 A | 2/1976 | Henkin |
| 3,962,917 A | 6/1976 | Terada |
| 4,003,396 A | 1/1977 | Fleischmann |
| 4,051,847 A | 10/1977 | Henkin |
| 4,078,554 A | 3/1978 | Lemaitre et al. |
| 4,186,735 A | 2/1980 | Henneman et al. |
| 4,188,946 A | 2/1980 | Watson et al. |
| 4,197,857 A | 4/1980 | Osborn |
| 4,200,094 A | 4/1980 | Gedeon et al. |
| 4,211,239 A | 7/1980 | Raemer et al. |
| 4,221,224 A | 9/1980 | Clark |
| 4,230,108 A | 10/1980 | Young |
| 4,341,867 A | 7/1982 | Johansen |
| 4,359,057 A | 11/1982 | Manzella |
| 4,368,740 A | 1/1983 | Binder |
| 4,386,604 A | 6/1983 | Hershey |
| 4,425,805 A | 1/1984 | Ogura et al. |
| 4,440,177 A | 4/1984 | Anderson et al. |
| 4,444,201 A | 4/1984 | Itoh |
| 4,463,764 A | 8/1984 | Anderson et al. |
| 4,572,208 A | 2/1986 | Cutler et al. |
| 4,598,700 A | 7/1986 | Tamm |
| 4,608,995 A | 9/1986 | Linnarsson et al. |
| 4,619,269 A | 10/1986 | Cutler et al. |
| 4,648,396 A | 3/1987 | Raemer |
| 4,658,832 A | 4/1987 | Brugnoli |
| 4,753,245 A | 6/1988 | Gedeon |
| 4,756,670 A | 7/1988 | Arai |
| 4,781,184 A | 11/1988 | Fife |
| 4,796,639 A | 1/1989 | Snow et al. |
| 4,850,371 A | 7/1989 | Broadhurst et al. |
| 4,856,531 A | 8/1989 | Merilainen |
| 4,909,259 A | 3/1990 | Tehrani |
| 4,914,959 A | 4/1990 | Mylvaganam et al. |
| 4,917,108 A | 4/1990 | Mault |
| 4,949,724 A | 8/1990 | Mahutte et al. |
| 4,955,946 A | 9/1990 | Mount et al. |
| 4,986,268 A | 1/1991 | Tehrani |
| 4,998,018 A | 3/1991 | Kurahashi et al. |
| 5,022,406 A | 6/1991 | Tomlinson |
| 5,038,773 A | 8/1991 | Norlien et al. |
| 5,038,792 A | 8/1991 | Mault |
| 5,042,500 A | 8/1991 | Norlien et al. |
| 5,042,501 A | 8/1991 | Kenny et al. |
| 5,060,506 A | 10/1991 | Douglas |
| 5,060,655 A | 10/1991 | Rudolph |
| 5,060,656 A | 10/1991 | Howard |
| 5,069,220 A | 12/1991 | Casparie et al. |
| 5,072,737 A | 12/1991 | Goulding |
| 5,081,871 A | 1/1992 | Glaser |
| 5,095,900 A | 3/1992 | Fertig et al. |
| 5,095,913 A | 3/1992 | Yelderman et al. |
| 5,117,674 A | 6/1992 | Howard |
| 5,119,825 A | 6/1992 | Huhn |
| 5,178,155 A | 1/1993 | Mault |
| 5,179,958 A | 1/1993 | Mault |
| 5,214,966 A | 6/1993 | Delsing |
| 5,233,996 A | 8/1993 | Coleman et al. |
| 5,282,473 A | 2/1994 | Braig et al. |
| 5,285,794 A | 2/1994 | Lynch |
| 5,293,875 A | 3/1994 | Stone |
| 5,299,579 A | 4/1994 | Gedeon et al. |
| 5,303,712 A | 4/1994 | Van Duren |
| 5,309,921 A | 5/1994 | Kisner et al. |
| 5,326,973 A | 7/1994 | Eckerbom et al. |
| 5,355,879 A | 10/1994 | Brain |
| 5,355,893 A | 10/1994 | Mick et al. |
| 5,357,972 A | 10/1994 | Norlien |
| 5,363,857 A | 11/1994 | Howard |
| 5,398,695 A | 3/1995 | Anderson et al. |
| 5,402,796 A | 4/1995 | Packer et al. |
| 5,419,326 A | 5/1995 | Harnoncourt |
| 5,425,374 A | 6/1995 | Ueda et al. |
| 5,450,193 A | 9/1995 | Carlsen et al. |
| 5,468,961 A | 11/1995 | Gradon et al. |
| 5,503,151 A | 4/1996 | Harnoncourt et al. |
| 5,570,697 A | 11/1996 | Walker et al. |
| 5,632,281 A | 5/1997 | Rayburn |
| 5,645,071 A | 7/1997 | Harnoncourt et al. |
| 5,647,370 A | 7/1997 | Harnoncourt |
| 5,676,132 A | 10/1997 | Tillotson et al. |
| 5,705,735 A | 1/1998 | Acorn |
| 5,754,288 A | 5/1998 | Yamamoto et al. |
| 5,789,660 A | 8/1998 | Kofoed et al. |
| 5,796,009 A | 8/1998 | Delsing |
| 5,800,360 A | 9/1998 | Kisner et al. |
| 5,816,246 A | 10/1998 | Mirza |
| 5,831,175 A | 11/1998 | Fletcher-Haynes |
| 5,834,626 A | 11/1998 | DeCastro et al. |
| 5,836,300 A | 11/1998 | Mault |
| 5,922,610 A | 7/1999 | Alving et al. |
| 5,932,812 A | 8/1999 | Delsing |
| 5,957,858 A | 9/1999 | Micheels et al. |
| 6,010,459 A | 1/2000 | Silkoff et al. |
| 6,044,843 A | 4/2000 | O'Neil et al. |
| 6,162,180 A * | 12/2000 | Miesel et al. ............... 600/481 |
| 6,309,360 B1 * | 10/2001 | Mault .................... 128/200.24 |

OTHER PUBLICATIONS

British Journal Of Anaesthesia, vol. 49, 1977 London (GB) pp. 575–587, J. A. Bushman et al. "Closed Circuit Anaesthesia."

IEEE Transactions on Biomedical Engineering, vol. 35, No. 9, Sep. 1988, pp. 653–659, Capek et al., "Noninvasive Measurement of Cardia Output Using Partial CO2 ReBreathing."

Clinics in Chest Medicine (Review), vol. 10, 1989, pp. 255–264, Heigenhauser et al., "Meausurement if Cardiac Output by Carbon Dioxide Rebreathing Methods."

Determination Of Nitric Oxide Levels By Fluorescence Spectroscopy, Gabor G. and Allon, N. in Biochemical, Pharmacological, and Clinical Aspects of Nitric Oxide, edited by B. A. Weissman et al, Plenum Press, New York, 1995, pp. 57.

* cited by examiner ically directed toward an
AIRWAY-BASED CARDIAC OUTPUT MONITOR AND METHODS FOR USING SAME This application claims benefit of Ser. No. 60/133,685 filed May 10, 1999.

FIELD OF THE INVENTION

The present invention relates to measurement of cardiac output of a patient. More specifically, the present invention relates to an apparatus and method for non-invasive cardiac output measurement of a subject utilizing a respiratory gas analyzer employing a flow sensor, an oxygen sensor, and a pulse oximeter which are interconnected to measure the cardiac output of the subject.

BACKGROUND OF THE INVENTION

U.S. Pat. No. 5,836,300 to Applicant discloses a respiratory gas analyzer for measuring the metabolic activity and the cardiac output of a subject including a bidirectional flow meter and a capnometer sensor interconnected by conduits and valving between a mouthpiece and a source of respiratory gases which can be a controlled source or the atmosphere. A computer receiving signals from the flow meter and the capnometer can then calculate the subject's metabolic activity. When valving is shifted, a portion of the exhaled gases are stored in the conduit so that upon inhalation, the subject inhales a substantial portion of rebreathed gases. The computer can then calculate the patient's cardiac output as a function of the changes in total carbon dioxide content of the exhaled gas before and after the valve is shifted from a direct input to a rebreathed position and the difference in end-tidal carbon dioxide between the two positions.

The cardiac output of a patient, that is the volume of blood ejected from the heart per unit time, is an important measured parameter in hospitalized patients. Currently, cardiac output is routinely measured by invasive techniques including thermal dilution using an indwelling pulmonary artery catheter. This technique has several disadvantages including the morbidity and mortality risks of placing an invasive intracardiac catheter, the infectious disease risks, significant expense and the fact that it provides an intermittent rather than a continuous measurement. A noninvasive, reusable cardiac output measurement device would substantially improve patient care and reduce hospital costs.

The partial rebreathing technique mentioned above is a known method for cardiac output measurement. As described in Kapec and Roy, "The Noninvasive Measurement of Cardiac Output Using Partial $CO_2$ Rebreathing," IEEE Transactions on Biomedical Engineering, Vol. 35, No. 9, September 1988, pp. 653–659, the method utilizes well known Fick procedures, substituting carbon dioxide for oxygen, and employing a sufficiently short measurement period such that venous carbon dioxide levels and cardiac output can be assumed to remain substantially constant during the measurement.

U.S. Pat. No. 4,949,724 to Mahutte et al. discloses a method and apparatus for continuously monitoring cardiac output by utilizing a modified Fick equation. The Mahutte et al. patent replaces $VO_2$ in the Fick equation by $VCO_2$ divided by a constant representative of the gas exchange ratio of a patient in order to eliminate inaccuracies associated with monitoring the rate of uptake of oxygen.

In its original form, the Fick method of measuring cardiac output requires blood gas values for arterial and mixed venous blood as follows:

$$C.O. = \frac{VO_2}{CaO_2 - CvO_2}$$

where C.O. is cardiac output, $VO_2$ is oxygen consumption, $CaO_2$ is the arterial oxygen content, and $CvO_2$ is the venous oxygen content.

By utilizing a respiratory analyzer with a fast-response oxygen sensor, the cardiac output can be determined based on the end-tidal oxygen concentration ($EtO_2$). End-tidal oxygen concentration is the lowest value of oxygen concentration in breath. The end-tidal oxygen concentration approximates the pulmonary capillary oxygen concentration.

Alternatively, at different points in time, it is also true that $$C.O. = \frac{VO_{2(1)}}{CaO_{2(1)} - CvO_{2(1)}} = \frac{VO_{2(2)}}{CaO_{2(2)} - CvO_{2(2)}}.$$

If the oxygen concentration of the inspired gas is temporarily increased or decreased, the change in alveolar oxygen concentration will cause a transient uptake or release of oxygen across the pulmonary capillaries, thereby resulting in a change in the measured $VO_2$ and arterial oxygen content ($CaO_2$). If these parameters are measured during an interval of time less than the circulation time (i.e., less than approximately thirty-fifty seconds), then the venous oxygen content ($CvO_2$) level remains essentially constant during this period and can be removed from the equation. Therefore, cardiac output can be determined based on the equation $$C.O. = \frac{\Delta VO_2}{\Delta CaO_2}$$

The use of these novel concepts in combination with the apparatus and method of the present invention therefore allows for the non-invasive measurement of cardiac output utilizing measurements of airway gases and arterial oxygen concentrations, both of which can be done by non-invasive techniques.

SUMMARY OF THE INVENTION

The present invention is accordingly directed toward an airway-based respiratory gas analyzer for measuring the cardiac output of a subject. In a preferred embodiment of the analyzer of the present invention, the analyzer includes a respiratory connector operative to be supported in contact with a subject so as to pass inhaled and exhaled gases as the subject breathes. A flow meter operatively connected to the respiratory connector generates electrical signals as a function of the volume of gases which pass therethrough and, in combination with the signals generated by an oxygen sensor, allows for the determination of oxygen consumption ($VO_2$) by integrating the flow and oxygen concentration signals over an entire breath. The oxygen sensor can also provide for the measurement of end-tidal ($EtO_2$) concentration. An oximeter provides measurements of the subject's oxygen saturation. A computation unit receives the output signals from the flow sensor, oxygen sensor and oximeter and calculates the cardiac output based on the generated signals.

An alternative mechanism for performing measurements of the subject's cardiac output includes the subject placing the mouthpiece of the analyzer into their mouth and breathing a first oxygen concentration for a first period of time. Typically, the source of respiratory gases is atmospheric air. As the subject breathes, oxygen consumption ($VO_2$) is determined as the integral of the flow and oxygen concentration signals over the entire breath. The oximeter provides a measurement of the subject's oxygen saturation which is utilized to calculate the subject's arterial oxygen content. After obtaining the measurement of the oxygen consumption ($VO_2$) and arterial oxygen content ($CaO_2$) over the first time period, the oxygen blender is caused to provide an increase or decrease in the airway oxygen concentration of the subject for a second period of time which is less than the subject's circulation time. The oxygen consumption ($VO_2$) and arterial oxygen content ($CaO_2$) are measured over this second time period on a breath-by-breath basis and are utilized in calculating the subject's cardiac output.

According to one aspect of the present invention, there is provided a respiratory gas analyzer for measuring cardiac output of a subject, said analyzer comprising:

a respiratory connector operative to be supported in contact with a subject so as to pass inhaled and exhaled gases as the subject breathes;

a flow sensor operatively connected to said respiratory connector adapted to generate electrical signals as a function of the volume of gases which pass therethrough;

an oxygen sensor for sensing the concentration of oxygen in the inhaled and exhaled gases, to thereby enable a determination to be made of the oxygen consumed by the subject during each breath;

conduits interconnecting said respiratory connector, said flow meter, and said oxygen sensor;

an oximeter for enabling a determination to be made of the concentration of oxygen in the subject's arterial blood; and a computer for receiving output signals from said flow sensor, said oxygen sensor, and said oximeter to calculate the cardiac output of the subject without the need for sensing the concentration of oxygen in the subject's venous blood.

According to one preferred embodiment of the invention described below, the analyzer is used in a two-measurement procedure, wherein the computer calculates the cardiac output (C.O.) of the subject according to the following equation:

$$C.O. = \frac{\Delta VO_2}{\Delta CaO_2}$$

wherein: $\Delta VO_2$ is the difference in said consumed oxygen in the two-measurement procedure, and $\Delta CaO_2$ is the difference in said arterial oxygen in the two-measurement procedure;

and wherein: the two-measurement procedure involves:
(a) a first measurement of said consumed oxygen and said arterial oxygen during a first time interval, and
(b) a second measurement, following a change in the oxygen content of the inhaled air, during a second time interval having a duration less than the blood circulation time of the subject.

According to a second described preferred embodiment, the computer calculates the cardiac output (C.O.) of the subject computer calculates the cardiac output (C.O.) of the subject according to the following equation:

$$C.O. = \frac{VO_2}{CaO_2 - CvO_2}$$

wherein: $VO_2$ is the oxygen consumed during a breath; $CaO_2$ is the concentration of oxygen in the subject's arterial blood; and $CvO_2$ is the concentration of oxygen in the subject's venous blood, which is assumed to be the same as the end-tidal oxygen concentration in the exhaled air.

Other features, advantages and applications of the present invention will be made apparent from the following detailed description of the preferred embodiments.

BRIEF DESCRIPTION OF THE DRAWINGS

Other advantages and applications of the present invention will be made apparent by the following detailed description of preferred embodiments of the invention. The description makes reference to the accompanying drawings in which.

DETAILED DESCRIPTION OF THE INVENTION

Figure 1:
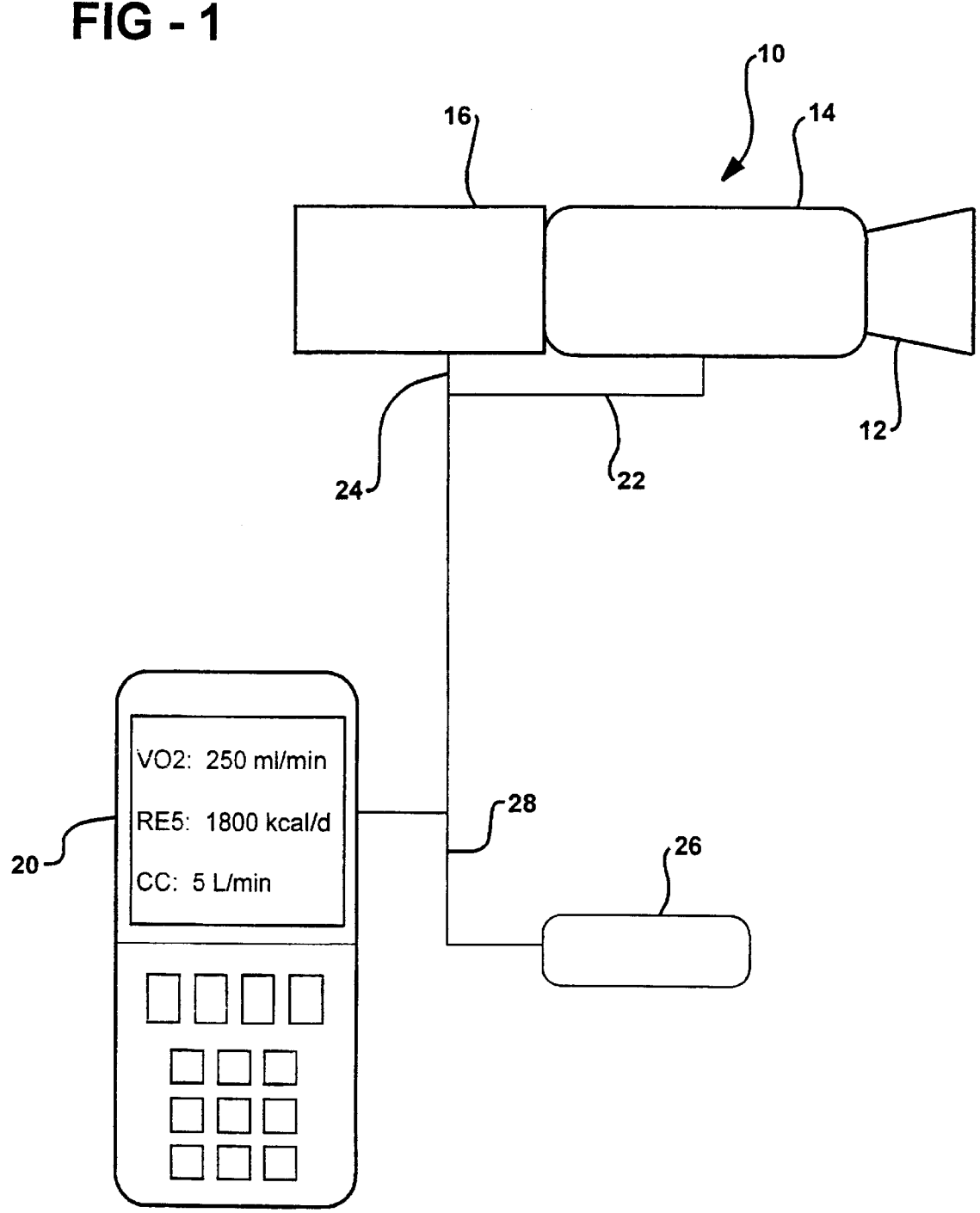
FIG. 1 is a schematic representation of a first embodiment of the present invention.

Referring to FIG. 1, a preferred embodiment of the present invention includes an airway-based cardiac output analyzer, generally indicated at 10, having a mouthpiece 12, a flow sensor 14, and a gas sensor 16. The flow sensor 14 and the gas sensor 16 are disposed in fluid communication with one another.

The mouthpiece 12 is adapted to engage the inner surfaces of a user's mouth, so as to form the sole passage for flowing respiratory gases into and out of the mouth. A nose clamp of conventional construction (not shown) can be employed in connection with the mouthpiece 12 to assure that all respiratory gas passes through the mouthpiece 12. In alternative configurations, a mask that engages the nose as well as the mouth of the user can be employed or an endotracheal tube could also be utilized.

The mouthpiece 12 is located adjacent to a bi-directional volume flow sensor 14. The flow sensor is preferably an ultrasonic flow meter such as an ultrasonic transit time flow meter such as that manufactured by NDD Medizintechnik AG, Zurich, Switzerland, and disclosed in U.S. Pat. Nos. 3,738,169; 4,425,805; 5,419,326; and 5,645,071. Preferably, the ultrasonic flow meter transmits and receives ultrasonic pulses along a path which is either parallel to or has a substantial component in the direction of the flow. The gas flow acts to advance or retard the flow of pulses so that the full transit time of the pulses is a function of the flow rate. Alternatively, the flow sensor 14 can be of the pressure differential type such as manufactured by Medical Graphics Corporation, St. Paul, Minn. under the trademark MEDGRAPHICS and of the general type illustrated in U.S. Pat. No. 5,038,773. Alternatively, other types of flow transducers such as pneumatics or spirometers could also be employed. The electrical output of the bi-directional flow sensor 14 is connected to a computation unit 20 through a conductive line 22.

The other end of the flow sensor 14 is connected to the gas sensor 16. The gas sensor 16 is preferably a fast-response (i.e. 50–80 millisecond response time), flow-through type oxygen sensor and is preferably of the fluorescent quench type as disclosed in U.S. Pat. Nos. 3,725,658; 5,517,313; and 5,632,958. The preferred embodiment can employ a sensor manufactured by Sensors for Medicine and Science, Inc., Germantown, Md. The electrical output of the gas sensor 16 is connected to the computation unit 20 through a conductive line 24. The computation unit 20 can include a source (not shown) for directing exciting radiation to a fluorescent coating disposed on the oxygen sensor 16 and sensing the resulting fluorescence intensity which is diminished as a function of the concentration of oxygen in the gas flowing over its surface to produce a direct measurement of oxygen concentration. The exciting radiation and fluorescent signal can be carried to the sensor 16 by an optical fiber (not shown).

A pulse oximeter 26 can be utilized to monitor oxygen saturation by pulse oximetry. The pulse oximeter 26 provides an output signal which is received by the computation unit 20 which is indicative of saturation percentage. The output signal of the pulse oximeter 26 is connected to the computational unit 20 through a conductive line 28. In a preferred embodiment, the pulse oximeter is preferably of the type manufactured by Datax-Ohlmeda, Louisville, Colo. Alternatively, for most healthy individuals, the pulse oximeter 26 can be omitted and the oxygen saturation can be assumed to be approximately 95–96%.

Figure 3:
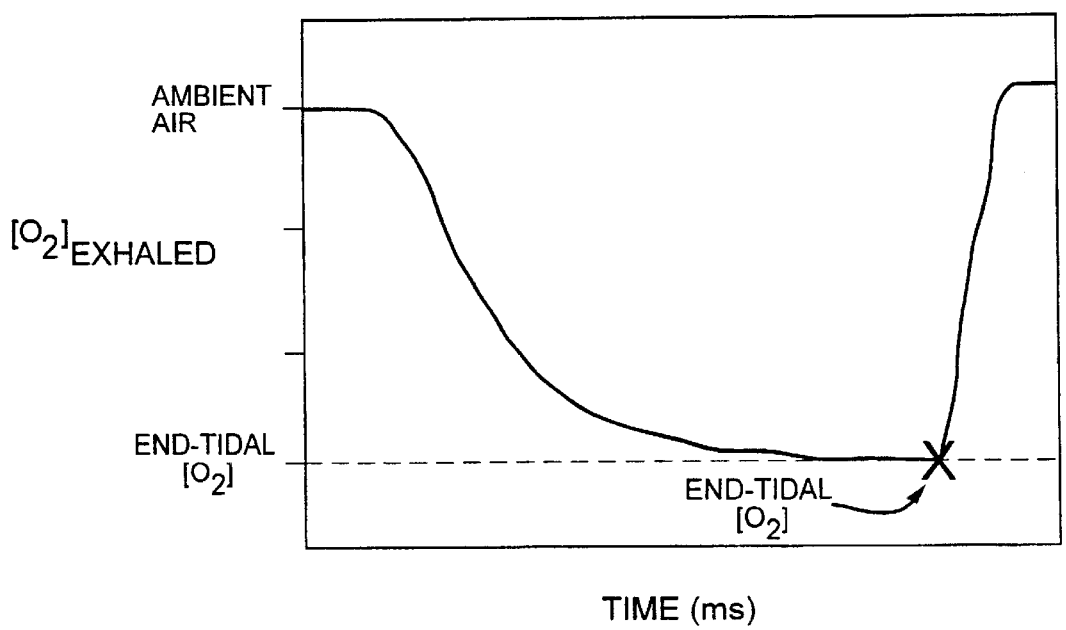
FIG. 3 is a graph of oxygen concentration over time measured in milliseconds to illustrate oxygen concentration as recorded with a fast-response oxygen sensor and is also illustrative end-tidal oxygen concentration.

Utilizing the Fick equation, in combination with the airway-based respiratory gas analyzer 10 having the flow sensor 14 and the fast-response oxygen sensor 16, allows for the determination of a subject's cardiac output by utilizing measurements of end-tidal oxygen concentration and $VO_2$. The airway-based gas analyzer 10 allows for the determination of end-tidal oxygen concentration ($EtO_2$) as illustrated in FIG. 3. If one assumes that $EtO_2 \approx PvO_2$ (dissolved venous oxygen concentration in the plasma), then using the $PvO_2$ and the hemoglobin concentration, the $SvO_2$ can be determined based on the oxygen dissociation curve. The pulse oximeter 26 can be used to obtain oxygen saturation movement so that based on the Fick equation of $$C.O. = \frac{VO2}{CaO_2 - CvO_2}$$

wherein $VO_2$ is measured by the airway based respiratory analyzer, $CaO_2$ and $CvO_2$ are determined according to the equations $CaO_2 = [(SaO_2)(Hgb)(1.36)+(PaO_2)(0.0031)]$ and $CvO_2 = [(SvO2)(Hgb)(1.36)+(PvO_2)(0.0031)]$, respectively, wherein $SaO_2$ is the oxygen saturation measurement obtained by pulse oximetry, Hgb is the hemoglobin concentration (which is entered as a known value or by direct measurement), and $PvO_2$ is obtained from the measurement of $EtO_2$. It is assumed that $EtO_2$ approximates $PvO_2$ and, if the $PvO_2$ and the hemoglobin concentrations are known, using the oxygen dissociation curve, $SvO_2$ can be determined. The pulse oximeter 26 measures $SaO_2$ (alternatively, $SaO_2$ and $PaO_2$ can be reasonably assumed).

Figure 2:
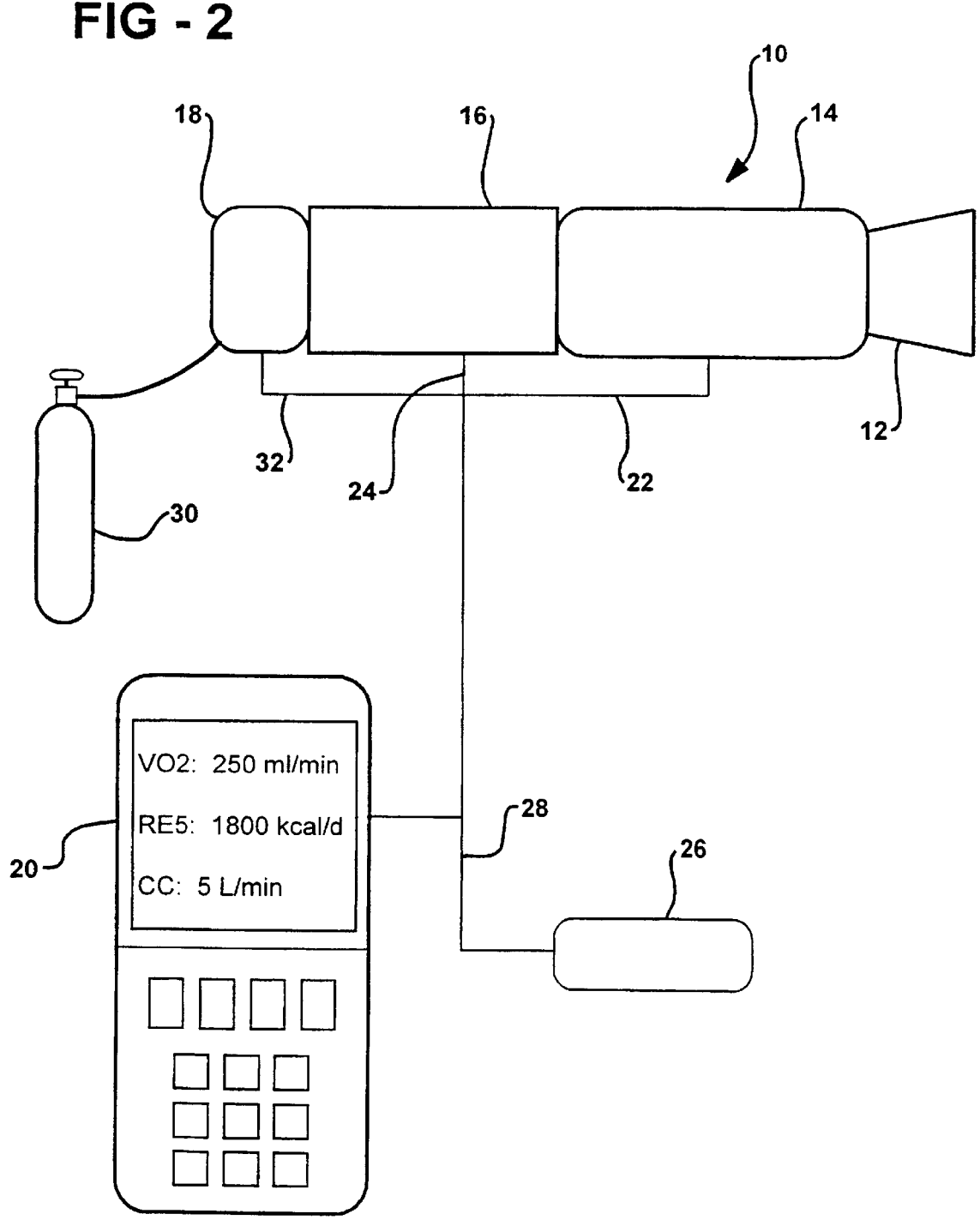
FIG. 2 is a schematic representation of a second embodiment of the present invention.

Referring to FIG. 2, in an alternative embodiment of the present invention is shown wherein like numerals represent like elements among the embodiments, a gas blender 18 is disposed directly adjacent to and in fluid communication with the gas sensor 16. The gas blender 18 is also in fluid communication with the atmosphere or a source and sink of respiratory gases. The gas blender 18 can also be connected to a ventilator or source of calibrated or known gases such as an external oxygen tank 30. The gas blender 18 is preferably computer controlled and is in electrical communication with the computation unit 20 through a conductive line 32. That is, the computation unit 20 can transmit signals to the gas blender 18 in order to modify, mix, or change the composition of the inhaled air passing through the cardiac output analyzer 10 to the subject. In other words, the gas blender 18 can be caused to allow an increase/decrease in the concentration of airway oxygen for a given or predetermined period of tim e .

In a further alternative embodiment, the pulse oximeter 26 can be replaced by a synchronized, side-port sampling oxygen sensor as is well known in the art. That is, a portion or sample of the gases flowing through the analyzer is directed via a port to an oxygen sensor.

The analyzer 10 can also incorporate an artificial nose and/or a bacterial filter as described in Applicant's previous patents or can incorporate a temperature sensor which provides a signal to the computation unit 20 to adjust the measurements as a finction of breath and external air temperature.

In operation, in order to non-invasively obtain a measurement of the cardiac output of a subject, the subject attaches the pulse oximeter 22 to a suitable portion of their body such as a finger or earlobe, the subject then places the mouthpiece 12 into their mouth and the oxygen consumption ($VO_2$) is determined as the integral of the flow of oxygen concentration signals over an entire breath. The arterial oxygen concentration is calculated according to the formula:

$CaO_2 = (SaO_2)(Hbg)(1.36)+(0.0031)(PaO_2)$ where $SaO_2$ is the oxygen saturation measurement obtained by the pulse oximeter 22, Hbg is the hemoglobin concentration (which is entered as a known value or obtained by direct measurement), and $PaO_2$ is the dissolved arterial oxygen concentration. After obtaining a stable measurement of $VO_2$ and $CaO_2$ over a first time period of approximately two to three minutes, the gas blender 18 is caused to increase/decrease the concentration of oxygen (preferably, at least a 10% change in $FIO_2$, e.g., 40% increased to 50%) supplied to the subject for a second time period less than the subject's circulation time of approximately thirty to fifty seconds. $VO_2$ and $CaO_2$ are monitored on a breath-by-breath basis during this time period and the cardiac output is then determined. Accordingly, the method and apparatus of the present invention take advantage of the phenomenon that if the oxygen concentration of the inspired gas is temporarily increased or decreased, the change in alveolar oxygen concentration will cause a transient uptake or release of oxygen across the pulmonary capillaries thereby resulting in a change in the measured $VO_2$ and arterial oxygen content ($CaO_2$). If these parameters are measured during an interval less than the circulation time (i.e., less than approximately thirty to fifty seconds), then the venous oxygen content ($CvO_2$) can be ignored and the cardiac output of the subject can be calculated based on the equation $$C.O. = \frac{\Delta VO_2}{\Delta CaO_2}$$

In view of the teaching presented herein, other modifications and variations of the present invention will readily be apparent to those of skill in the art. The discussion and description are illustrative of some embodiments of the present invention, but are not meant to be limitations on the practice thereof. It is the following claims, including all equivalents, which defines the scope of the invention.

What is claimed is:

1. A respiratory gas analyzer for measuring cardiac output of a subject, said analyzer comprising:
   a respiratory connector operative to be supported in contact with a subject so as to pass inhaled and exhaled gases as the subject breathes;
   a flow sensor operatively connected to said respiratory connector adapted to generate electrical signals as a function of the volume of gases which pass therethrough;
   an oxygen sensor for sensing the concentration of oxygen in the exhaled gases;
   means for determining the concentration of oxygen in the inhaled gases and generating a signal representative of the oxygen consumed by the subject during each breath;
   conduits interconnecting said respiratory connector, said flow meter, and said oxygen sensor;
   an oximeter for enabling a determination to be made of the concentration of oxygen in the subject's arterial blood; and
   a computer for receiving output signals from said flow sensor, said signal representative of the oxygen consumed by the subject during each breath, and said oximeter to calculate the cardiac output of the subject without the need for sensing the concentration of oxygen in the subject's venous blood.

2. The analyzer of claim 1, wherein, in a two-measurement procedure, said computer calculates the cardiac output (C.O.) of the subject according to the following equation:

$$C.O. = \frac{\Delta VO_2}{\Delta CaO_2}$$

wherein: $\Delta VO_2$ is the difference in said consumed oxygen in the two-measurement procedure, and $\Delta CaO_2$ is the difference in said arterial oxygen in the two-measurement procedure;

and wherein: the two-measurement procedure involves:
   (a) a first measurement of said consumed oxygen and said arterial oxygen during a first time interval, and
   (b) a second measurement, following a change in the oxygen content of the inhaled air, during a second time interval having a duration less than the blood circulation time of the subject.

3. The analyzer of claim 2, wherein said computer calculates the cardiac output (C.O.) of the subject according to the following equation:

$$C.O. = \frac{VO_2}{CaO_2 - CvO_2}$$

wherein: $VO_2$ is the oxygen consumed during a breath; $CaO_2$ is the concentration of oxygen in the subject's arterial blood; and $CvO_2$ is the concentration of oxygen in the subject's venous blood, which is assumed to be the same as the end-tidal oxygen concentration in the exhaled air.

4. The analyzer of claim 1 further including a gas blender operatively connected in fluid communication with said conduits for changing the concentration of the oxygen in the inhaled gases.

5. The analyzer of claim 1, wherein said oxygen sensor is a fluorescence quench oxygen sensor.

6. The analyzer of claim 1, wherein said oxygen sensor is a side-port sampling oxygen sensor.

7. The analyzer of claim 1, wherein said respiratory connector is a mouthpiece.

8. The analyzer of claim 4, wherein said flow sensor, said oxygen sensor, said oximeter, and said gas blender comprise a mechanism for transferring output signals therefrom to said computer.

9. The analyzer of claim 8, wherein said mechanism comprises a conductive line.

10. The analyzer of claim 4, wherein said gas blender is operatively connected to a source of respiratory gas.

11. The analyzer of claim 10, wherein said source of respiratory gas is the atmosphere.

12. The analyzer of claim 10, wherein said source of respiratory gas is a source of oxygen.

13. A method for non-invasive cardiac output measurement of a subject, said method comprising the steps of:
   (a) determining oxygen consumption of a subject;
   (b) determining end-tidal oxygen concentration of the subject; and
   (c) calculating the cardiac output of the subject based on the oxygen consumption and the end-tidal oxygen concentration determined in steps (a) and (b).

14. The method of claim 13, wherein the cardiac output (C.O.) is calculated according to the following equation:

$$C.O. = \frac{VO_2}{CaO_2 - CvO_2}$$

wherein: $VO_2$ is the oxygen consumed during a breath; $CaO_2$ is the concentration of oxygen in the subject's arterial blood; and $CvO_2$ is the concentration of the oxygen in the subject's venous blood and is determined in accordance with the equation $$CvO_2 = (SvO_2)(Hbg)(1.36) + (0.0031)(PvO_2)$$

wherein $SvO_2$ is the oxygen saturation, Hbg is the hemoglobin concentration, and $PvO_2$ is the dissolved venous plasma oxygen and is assumed to be the determined end-tidal oxygen concentration of the subject.

15. The method of claim 14, wherein arterial oxygen content is determined in accordance with the equation $$CaO_2 = (SaO_2)(Hbg)(1.36) + (PaO_2)(0.0031)$$

wherein $SaO_2$ is the arterial oxygen saturation, Hbg is the hemoglobin concentration, and $PaO_2$ is the dissolved arterial oxygen concentration.

16. A method for non-invasive cardiac output measurement of a subject, said method comprising the steps of:
   (a) determining oxygen consumption and arterial oxygen content of a subject over a first time interval and for a first oxygen concentration;
   (b) changing the oxygen concentration breathed by the subject for a second time interval wherein the second time interval is less than the circulation time of the subject; and
   (c) calculating the cardiac output of the subject based on the relative change in both oxygen consumption and arterial oxygen content determined in steps (a) and (b).

17. The method of claim 16, wherein the cardiac output (C.O.) of the subject is calculated according to the following equation:

$$C.O. = \frac{\Delta VO_2}{\Delta CaO_2}$$

wherein $\Delta VO_2$ is said relative change in oxygen consumption and $\Delta CaO_2$ is said relative change in arterial oxygen.

18. The method of claim 16, wherein said first time interval ranges from approximately one to five minutes.

19. The method of claim 18, wherein said first time interval ranges from approximately two to three minutes.

20. The method of claim 16, wherein said second time interval ranges from approximately twenty seconds to sixty seconds.

21. The method of claim 20, wherein said second time interval ranges from approximately thirty seconds to fifty seconds.

22. The method of claim 16, wherein the oxygen concentration in step (b) is increased from approximately 40 percent to approximately 50 percent.

* * * * *

UNITED STATES PATENT AND TRADEMARK OFFICE
CERTIFICATE OF CORRECTION

PATENT NO. : 6,517,496 B1
DATED : February 11, 2003
INVENTOR(S) : James R. Mault It is certified that error appears in the above-identified patent and that said Letters Patent is hereby corrected as shown below:

Title page,
Item [56], References Cited, OTHER PUBLICATIONS, replace "Cardia" with -- Cardiac --; and replace "Measurement if" with -- Mesurement of --.

Column 3,
Line 65, delete second occurrence of "computer calculates the cardiac output (C.O.) of the subject"

Column 5,
Line 26, replace "Ohlneda" with -- Ohmeda --.

Column 6,
Line 14, replace "tim e" with -- time --.

Column 7,
Line 17, delete ";" and insert -- , to thereby enable a determination to be made of the oxygen consumed by the subject during each breath; --.
Line 18-21, delete lines 18-21
Line 27-28, delete "said signal representative of the oxygen consumed by the subject during each breath,"

Signed and Sealed this

Twentieth Day of April, 2004

JON W. DUDAS
*Acting Director of the United States Patent and Trademark Office*